United States Patent [19]
Yasaka et al.

[11] 3,970,996
[45] July 20, 1976

[54] APPARATUS FOR COLLECTING MEDICAL DATA

[75] Inventors: Toshio Yasaka; Ryuzo Ito; Sadao Takagi, all of Tondabayashi, Japan

[73] Assignee: Perfect Liberty, Japan

[22] Filed: Jan. 7, 1974

[21] Appl. No.: 431,232

[30] Foreign Application Priority Data
Feb. 28, 1973  Japan.............................. 48-23233

[52] U.S. Cl. ............................................. 340/172.5
[51] Int. Cl.$^2$ ...................... G06F 3/02; G06F 3/04; G06F 3/12
[58] Field of Search ............ 340/172.5; 235/61.6 R, 235/61.7 R, 61.12, 150, 151; 128/2 R, 2 D, 2.05 R

[56] References Cited
UNITED STATES PATENTS

| | | | |
|---|---|---|---|
| 3,374,461 | 3/1968 | Anderholm et al. | 340/172.5 |
| 3,566,365 | 2/1971 | Rawson et al. | 340/172.5 |
| 3,566,370 | 2/1971 | Worthington, Jr. | 340/172.5 |
| 3,597,742 | 8/1971 | Philipps et al. | 340/172.5 |
| 3,618,592 | 11/1971 | Stewart | 128/2.05 R |
| 3,675,640 | 7/1972 | Gatts | 128/2 D |
| 3,725,866 | 4/1973 | Oldfield, Jr. et al. | 340/172.5 |
| 3,727,190 | 4/1973 | Vogelman et al. | 340/172.5 |
| 3,818,454 | 6/1974 | Yaccino | 340/172.5 |
| 3,831,006 | 8/1974 | Chaffin et al. | 235/61.7 R |
| 3,839,708 | 10/1974 | Bredeson et al. | 340/172.5 |

*Primary Examiner*—Gareth D. Shaw
*Assistant Examiner*—John P. Vandenburg
*Attorney, Agent, or Firm*—Hill, Gross, Simpson, Van Santen, Steadman, Chiara & Simpson

[57] ABSTRACT

An apparatus for collecting and recovering medical data which allows a number of different patients to be identified by an ID card or an ID label and has a plurality of keyboard printing units which receive medical data from the particular patient and includes a memory which receives the individual medical data relative to the individual patient identified by the patient's number and the examination number and includes a system for transferring the data in usual form to an output unit after the necessary data has been recorded in the memory. The apparatus further includes a control unit for controlling the input and output units as well as the memory unit and includes error correcting systems.

3 Claims, 8 Drawing Figures

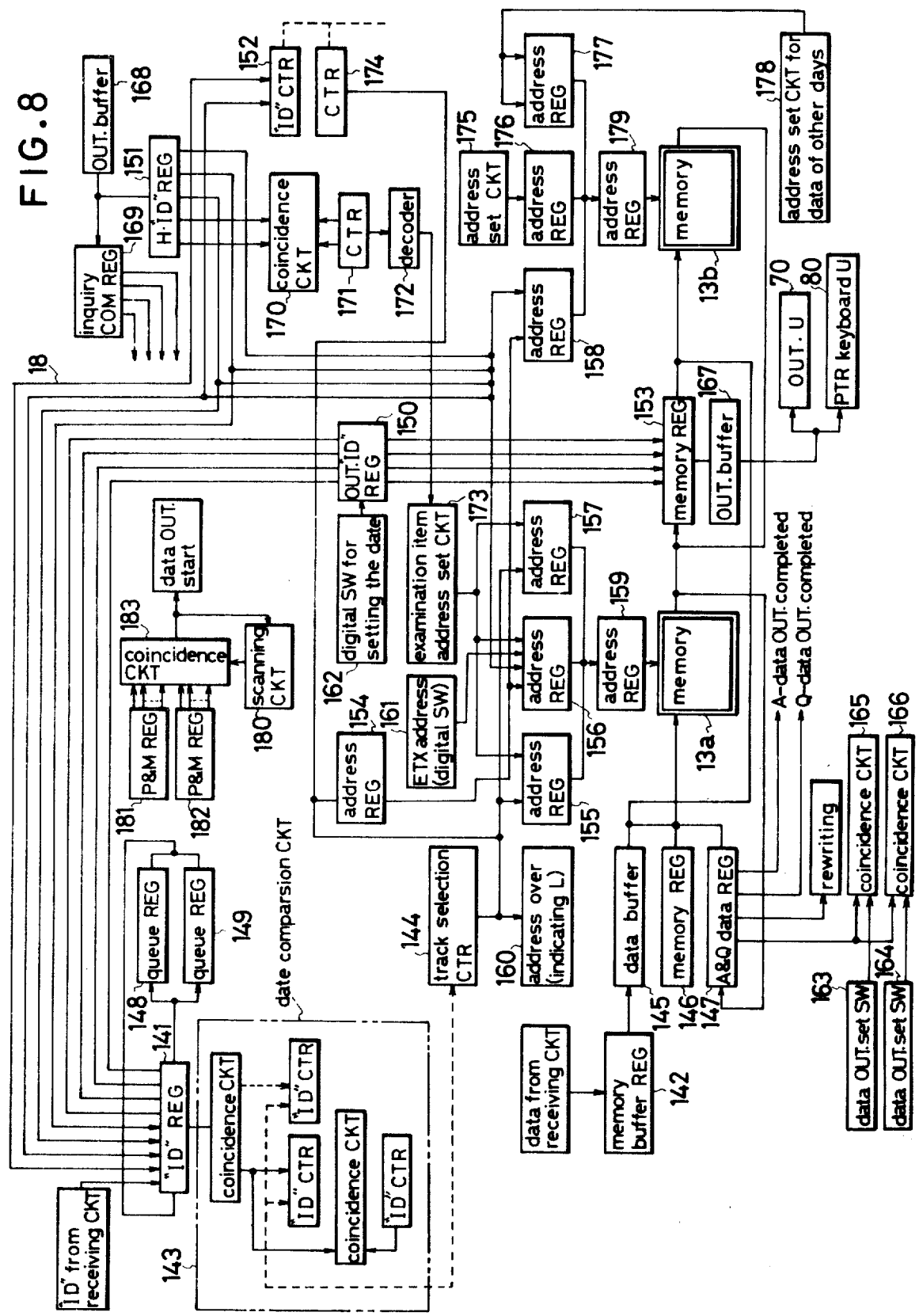

APPARATUS FOR COLLECTING MEDICAL DATA

BACKGROUND OF THE INVENTION

1. Field of the Invention

This invention relates in general to medical data accumulating and recording systems and in particular to a novel recording and storage system.

2. Description of the Prior Art

Prior to this invention, overall diagnosis systems for automated multiphasic health testing systems generally utilized general purpose electronic computers for processing the data. However, the medical data which can be obtained from the results of physical examinations and diagnosis of physicians received from a number of examination facilities and from a variety of automatic examination equipment might be in the form of punched cards, marked cards, or marked sheets which carry codes for identifying the individual patient. Data media such as paper tapes and magnetic tapes produced by automatic examination equipment are ordinarily punched or marked manually and are carried to the elctronic computer room by the operator and placed in the card reader, marked sheet reader, paper tape reader, or magnetic tape reader of the computer. However, with such methods a great deal of processing time is required as well as a great possibility of errors being introduced into the system by the manual operation of the operators which might, for example, mispunch, miswrite, or lose data during transit. Thus, there is a great need to develop medical data storage, recording, and recovery apparatus which operates automatically and utilizes the development of automatic examination and measuring devices and instruments which can be directly connected to the data storage and retrieving system without requiring extensive use of manual operations.

SUMMARY OF THE INVENTION

The present invention relates to apparatus and system for collecting medical data as for example, "on line" medical data which is generated as the result of a medical examination and diagnosis of a patient who might, for example, be examined in a health control center where a number of medical examinations and a variety of diagnosis are performed by physicians in short periods of time. In other words, the present system would be very useful in medical centers which examine and diagnose large numbers of so-called generally healthy people and where the individual doctors do not spend a great deal of time on each individual test. It is very desirable at the present time to develop automatic techniques for medical examination. This is because of the automatic measuring and examining devices and instruments which might, for example, produce electrical output signals that can be directly fed into electronic computers and electronic data processing equipment with suitable interface equipment. The physical examination and diagnosis made by medical doctors are still difficult to interface into the automated processing system, and the present invention provides for efficient and rapid methods of accomplishing this. It is also desirable that in response to inquiries, data can be withdrawn in real time in a desired form such as paper tape, magnetic tape, pictures, or one or more visual recordings. It is also desirable that the outputs and data be of a form and type to satisfy a particular purpose and that such particular type be produced at the output without requiring a manual setting of the machine.

It is therefore an object of this invention to provide a data collecting system which allows improved and easy input of data from input units installed in a variety of medical examination and diagnosis rooms, and which is connected to output unit for producing medical data of the type which allows effective and instantaneous use of the data, and which is connected to a printer keyboard unit used for making inquiry.

Another object of this invention is to provide a medical data collecting system having a circuit which is capable of being set to an individual patient's identification number, and is capable of when used with the data collecting system, determining the address where the medical data of the individual person will be recorded and stored with the individual patient number serving as a common key for medical data recording.

Yet another object of this invention is to provide an interface unit which is so designed and used to be adapted to the function of a variety of data processing units attached to a variety of automatic examination devices for the purpose of transferring electrical signals from the automatic examination devices which have been produced as examination results to a signal collecting unit. An interface unit has been designed and used to furnish an individual patient's discrimination number in the form of an electrical signal to cause functioning of a variety of data processing units attached to the variety of automatic examination devices.

A further object of this invention is to provide a keyboard-printing device for medical data which is connected to the signal collecting unit and which has means for applying the individual discrimination patient number and the individual discrimination number of the operator in the case where atuomatic examination devices are not allowed to be used. The examination and doctor's diagnosis performed with ordinary facilities can be used with the data collecting system to identify individual persons being examined. Keyboards may be arranged according to the lists of diagnosis of a variety of examination facilities and doctors, thus eliminating the possibility that the operator may change it to another code, so that individual keys on which are engraved diagnosis of examination results in stepped manner, permit individual medical data to be provided as input.

A further object of this invention is to provide a data collecting system which, when the required sets of medical data records from a number of medical data input units are collected, automatically produces medical data records in a form which contains the individual patient's discrimination number in real time operation, and produces in real time the useful medical data records upon inquiry.

Electronic computer system used for automated multiphasic health testing system overall examination systems are ordinarily designed for general application purpose and have many excellent functions. However, when used for limited applications, the operation if often uneconomical and is not suited for carrying out the above-mentioned specific functions.

Accordingly a still further object of this invention is to design a variety of input units for medical data for a data collecting system which restricts unnecessary functions, in order to minimize expense for data processing.

This invention provides a medical data collecting system for collecting "on line" medical data, and eliminates the drawbacks inherent in the conventional systems.

One of the features of this invention is the provision of keyboard-printing units for medical data, such as the well-known keyboard-printers in order to accept at appropriate locations the medical data such as exmination results obtained by the examination facilities and doctor's diagnosis. The medical data keyboard-printer includes the "ID" card reader suited for taking and interpreting the ID card such as code card for feeding the individual discrimination number (hereinafter called ID) to discriminate the individual person being examined to facilitate the storage of medical data obtained in the automated overall examination system. The concept of an individual discrimination number for each person being examined replaces the discrimination number of the conventional examined material, but serves to directly link the human blood vessels with the machines used for examination, eliminating the drawbacks that the examined material and person examined will be separated, which have been inherent in the conventional methods. In other words, the ID card is one unique to the individual person who is to be examined. The keyboard-printer for the medical data is of a specific construction and has a number of keys on which are engraved quantitative expressions or staged expressions or character classifications on examination results for allowing appropriate arrangement and disposition of medical data such as examination results obtained in examination facilities in overall examination system. Also doctor's diagnosis for every item of examination and diagnosis can be encoded without requiring conversion into other codes which might result in errors caused by the operator. Also included is the data keyboard for medical data for retrieving and producing the electric signals temporarily according to the individual conditions being set by the operation board key, ID card reader, operator card reader, the logic circuits which respond to indicate the electrical signals of the ID card, operator card, medical data keyboard, operation switch, and operator board key. In addition, an indicator lamp and indicator tube, or logic circuit which indicates the electrical signal from the signal collector unit, and a printer for producing the data received as a visual record in the field, and a control circuit for transferring the data to the signal collecting unit are provided.

The operation switch is protected by a cover which is generally locked so that it can be operated only by those who are trained to operate the system. Also, medical data keyboard-printers are available in which input operation can be simplified in such a manner that for medical data, data keys to be used in every normal examination and diagnosis are set beforehand, and data keys for manifesting abnormal items only when the results of examination and diagnosis indicate abnormal conditions are set. The keyboard-printer for medical data can be set to receive medical data inputs, such as examinations of urea, feces, eyesight, blood pressure, study of diagnosis, diagnosis of uterus cells, diagnosis on X-ray photos of chest and upper digestive systems, and the analysis of photos by naked eye, where automatic devices are not available for connection to the data collecting systems.

The apparatus of this invention is connected between a variety of automatic examination devices which perform examinations automatically and produces medical data. Furthermore, the apparatus of this invention is equipped with an input buffer storage memory which corresponds to the amount of data produced by the individual automatic examination devices, operation keys, logic circuit and indication lamps for indicating the electrical signals from the operation keys. Interface units including logic circuit and indication lamps which respond to indicate the electrical signals from the signal collecting units are provided. The apparatus of this invention is further provided with an interface unit including the ID card reader suited for accepting and reading ID cards where a variety of data processing units are attached to automatic examination devices. An interface unit having analog-to-digital converter for converting a number of analog signals into digital signals, is also provided. The interface unit is applicable to the automatic examination devices such as automated multiphasic blood analyzer, automated blood cell counters, automated blood sedimentation rate analyzers, automatic ECG analyzers, lung function data processing units, and automated audiometry examination devices. The individual medical data keyboard-printers and interface units are connected to the receiving circuit of respective data collecting units, and the respective units provide address information based on ID codes responsive to many electrical signals, and apply these respective signals to the memory channels of the signal collecting unit having addresses corresponding to the address information given respective signals. Such control is accomplished by the control circuits of the signal collecting unit.

Another feature of this invention is the provision for receiving circuit which responds to each channel and is connected to the input unit for each medical data, control circuit for controlling the inputs and outputs of a number of electric signals, peripheral circuits of memory units, memories $D_1-D_n$ including memory domain for memorizing medical data and storing temporarily the output data, and signal collecting unit including operating apparatus. The signal collecting unit has a logic circuit and counter indicating mechanism for indicating the number of data of individual medical data records received from the input units for medical data, logic circuit and indicating mechanism for detecting a variety of errors at the time of input or output, and logic circuit and indicating mechnism for indicating the operation of the data collecting system as well as many operating mechanisms. The receiving circuit of the signal collecting unit contains the interface, gate circuit and selection circuit. The signal collecting unit also has a group of setting switches $S_Q$ and $S_A$ for automatically producing the medical data records, and a logic circuit produces useful medical data records from the output units responsive to a variety of setting conditions. The signal collecting unit furthermore includes many power supplies, digital switches corresponding to the number of input units for medical data and for setting the address of the memory unit. Digital switches for setting the data, switch and logic circuit for rendering all addresses of the memory to be a spaced state, switch and logic circuit for causing the output unit to produce all data records stored in the memory are also provided. A number of electrical signal lines connect medical data input units to the signal collecting units and are shielded for preventing interference of electrical noise which is generated by neighboring devices. Also, for safety in transferring the electrical signals, they are transferred in the form of a DC voltage of a magnitude of about 12 volts rather than in the form of pulse signals. Individual units can be set up as to prevent external noise interference.

Yet another feature of this invention is the provision for an output unit connected to and controlled by the signal collecting unit. Also, the output unit contained in the keyboard-printer which is connected to the signal collecting unit can be utilized by providing a switch. The output unit is connected to the memory unit peripheral circuits of the signal collecting unit and the control circuit. The keyboard printer is connected to the memory unit peripheral circuits of the signal unit and to the control circuit, and the examination numbers and the specific addresses of the memory are set for every individual patient discrimination numbers and the examination items selected by the keyboard-printer are combined appropriately in order to actuate the signal collecting device, so that data records of the memory are supplied to the keyboard-printer in the form of a command.

Yet another feature of this invention is the provision for a card reader which accepts medical data punched or marked on the standard 80 column card which has been designed specifically for storing a variety of medical data for use during emergencies when the input unit for medical data connected to the signal collecting unit is inoperative. At such times, the card reader transfers the medical data records to the signal collecting unit. The card reader contained in the printer keyboard is connected to the receiving circuit of the signal collecting unit and is used in the same way as the medical data input unit.

A still further feature of this invention is the provision of a communications control unit connected between the signal collecting unit and a modulator which is connected to the communications circuits, and which performs control and transfer of data between the signal collecting unit and the specific portion of the electronic computer system.

A further feature of this invention is found in the provision for a data collecting system which has more than 15 medical data input units and wherein the receiving circuits of the signal collecting unit operate a real time as inputs and outputs are furnished by many operators. Hence the selection circuit of the receiving circuits accepts the request for sending data in the order requested, and transfers the data to said address of the memory unit through individual gate circuits. The waiting time on the medical data input unit side is selected to be about 20 milli-seconds on the average, so that "waiting time" is hardly recognized by the operators, and the system is set up as to perform real time operation as regards outputs from the automatic examination devices. The control circuit of the signal collecting unit contains a protection circuit which writes in duplicate the data with respect to the address of the memory and prevents the data which have already been written from being lost; and prevents inadvertently writing two different data in the same address such as when data is sent from the same medical data input unit by using the same ID card twice. In this case, an error signal is returned to the medical data input unit which requests that the operator make correction. When it is required to amend or change the data records which have already been written, over-ride writing switches are contained in individual medical data input units can be set to allow rewriting. Moreover, a variety of medical data records of the overall examination system have been so set as to be produced automatically from the output unit in useful form for every individual being examined for various purposes.

Also, the ID card used commonly in the overall examination system and the above-mentioned medical data collecting system have a BCD code of 1.2.4.8. and have an individual person discrimination code constituted by a total of six digits; i.e., date, class number, and individual number in class, each set of two digits starting from the highest (or left) digit. When it is intended to input the medical data, the ID card possessed by the individual person is placed into the ID card reader. As for the automatic examination devices, the data is read from the ID card or from the ID label having codes equal to the ID card, and the data is collected in the same way as mentioned above. Hence specific addresses of the individual persons are set in the memory unit with the ID code as a key.

The units mentioned above have been set to meet the objects mentioned above. Owing to the above-mentioned setup, technical staffs engaged in the overall examination system are allowed to have space and time for offering more sophisticated services to the persons being examined, thereby contributing to the increased processing capability of the entire examination system. In addition accidents relating to the data during the data collecting operation which have often occurred in the past are reduced or eliminated with this invention.

Furthermore, owing to the employment of on-line real-time medical data collecting system, it is possible during overall examination and diagnosis by the doctor, to offer to the doctors more useful medical reference information based on medical data such as examination results and study of diagnosis, and in addition, sice it is possible to more effectively utilize the overall data including medical data of the diagnosis obtained by the doctor at the time of interview between the doctor and the person being examined, more competent medical services are offered to the person being examined.

Other objects, features and advantages of the invention will be readily apparent from the following description of certain preferred embodiments thereof, taken in conjunction with the accompanying drawings, although variations and modifications may be effected without departing from the spirit and scope of the novel concepts of the disclosure, and in which:

BRIEF DESCRIPTION OF THE DRAWINGS

FIG. 8 is a block diagram illustrating the memory and memory peripheral equipment showing the connection of the signal collecting unit, output unit, and the printer-keyboard unit.

DESCRIPTION OF THE PREFERRED EMBODIMENTS

Figure 1:
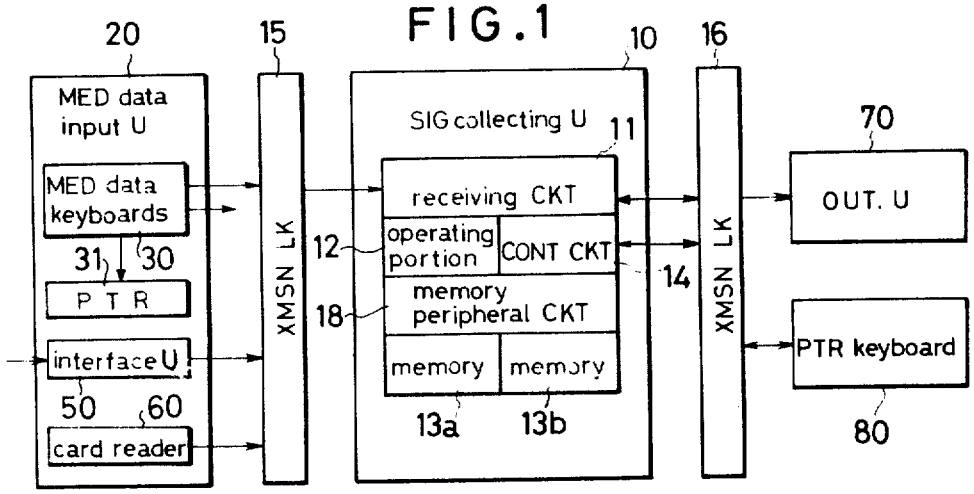
FIG. 1 is a block diagram of the on line medical data collecting system of the invention.

FIG. 1 shows a block diagram of the on-line medical data collecting system which is an embodiment of this invention. Referring to FIG. 1, signal collecting units 10 are connected via appropriate transmission links 15 to the medical data input units 20. Output unit 70 is also connected to unit 10 and the printer keyboard 80 via appropriate transmission links 16. Electrical signals from the individual medical data input units 20 are sent to the signal collecting unit 10 through a group of electrical cables of the links 15 connected to the input units 20. In this embodiment, the medical data input units 20 includes 10 units from medical data keyboards 30 and a printer 31, a card reader 60, and six interface units 50 which are connected to an automatic examination device or data processing unit which accepts medical information and produces it in a useful form.

Medical data keyboards 30 and/or interface units 50 may be connected to the transmission link 15 as long as their total number is less than four units. The signal collecting unit 10 gives the address for a particular device, i.e., examination address for discriminating examination items, to the individual medical data input units 20 connected to the signal collecting unit 10.

Further, individual units and the signal collecting unit are linked together for selected periods of time, so that information is transferred during these periods of time from the individual units to the signal collecting unit. Although the individual units are connected to the signal collecting unit at all times, the transfer of information is permitted only during the selected periods of time. The ID code which is an individual discrimination number for identifying an individual person being tested and is transmitted before the medical information from the medical information input units 20, and this causes the signal collecting unit 10 to operate so that the data is recorded in the specified address of the memory associated with that person of the signal collecting unit 10. Hence the ID of a person being examined serves as a common key in the data collecting system for accepting and producing medical information. The signal collecting unit 10 has a receiving circuit 11, an operating portion 12, a control circuit 14, a memory peripheral circuit 18 and memory units 13a, 13b.

In an embodiment of this invention, useful information produced from the output unit 70 is transferred from the input unit of the central data communications system to the central computer. The output unit has a paper-tape punch machine as well as a main unit and an auxiliary unit. A card punch machine or a communications control unit may be also connected. A printer with keyboard 80 produces in real time and in useful form the medical data recorded in the signal collecting unit upon inquiry. Printer 80 is also connected to the signal collecting unit 10. The printer - keyboard 80, however, may be conventional type for on-line applications. The card reader 60 and a paper-tape puncher which is an auxiliary device of the output unit 70 are contained in the printer-keyboard 80 and each are connected to the signal collecting unit 10.

Figure 2:
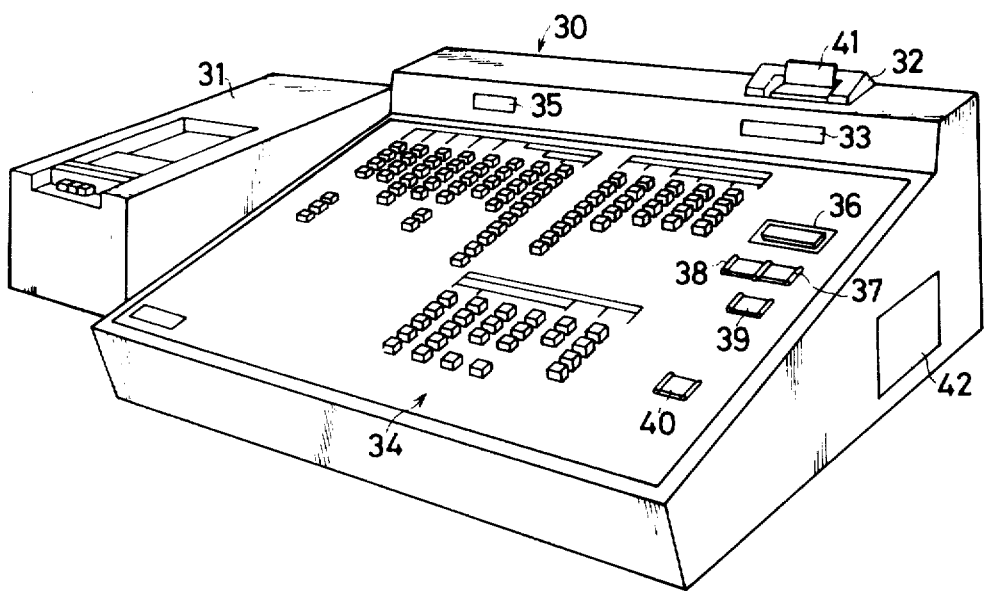
FIG. 2 is a perspective view illustrating the medical data keyboard-printer for urea examination which is one of the medical data input units of the invention.

FIG. 2 is a perspective view of an embodiment of the medical data keyboard 30 of this invention. FIG. 2 shows an example of units, some of which have 10 selectors. Other units have smaller number of selectors and medical data keys 34 allow specific tests to be selected. Medical data keyboard-printer 30 transmits electrical medical information to the signal collecting unit 10 and has a printing unit 31 which stores visual records. The printing unit 31 is a conventional digital printing unit.

An ID card reader 32 accepts ID card 41 for identifying individual persons being tested and reads the ID code. If the ID card 41 is put into the ID card reader 32, the individual number contained in the ID card is indicated on the indicator tube 33 on the panel to confirm to the operator the person being tested. At the same time, preparation completion lamp 37 turns on at which time the medical data keys 34 can be set to the desired tests. In an embodiment of this invention, operator cards need not be used. A variety of medical data keys 34 for examination results, study of diagnosis, X-ray photo diagnosis, naked-eye diagnosis, and pathological diagnosis, are provided and are of the indicator type. In units which have a large number of medical data keys 34, those keys which show normal examination results are set automatically and only certain additional keys are set for abnormal data. When the keys for showing abnormal conditions are set, the number of items set are indicated on the indicator tube 35 and can be observed by the operator. With other units, the keys have to be set manually for all tests and transmission of signals is not permitted unless the medical data keys 34 on all individual units are set. Each test unit includes a mechanism which allows setting of only one key in that unit.

Medical data records of the data key which is set is transmitted to the signal collecting unit 10 and is stored in electrical form. The ID card of the next person is inserted into the card reader 60. Indication type keys for operation control and indication lamps are also provided. A transmission key 40 transmits the medical data records to the signal collecting unit 10 when the ID card 41 and medical data keys 34 have been completed. Error lamp 36 informs the operator of errors when the predetermined conditions are not satisfied due to errors even though the medical data have been transmitted to the signal collecting unit 10. Also provided are power supply lamp 38 and a key 39 for checking with a lamp all keys of said indication type. Inside the cover 42 at the side of the unit 30 are contained a power supply switch, a selection switch, an over-ride write switch, and a general reset switch. The cover 42 is generally locked and should be operated only by particular individuals who have been trained to operate the machine.

An ID card 41 of a person who will be examined contains the coded individual identification number of the person and is read by the ID card reader 32 and an electrical signal is transmitted to the signal collecting unit 10. ID labels may also be read. The label is places in a sample cup contained in a bag for the person who will be examined, and the individual identification number of the ID label is read by the ID reader either before or after the medical data have been obtained, and is transmitted to the signal collecting unit 10 together with the medical data records. The ID code causes the signal collecting unit 10 to place the data in the memory unit to retain it at the correct address and protects individual medical data records contained in the memory units. The over-ride switch of the medical data input units temporarily halts operation of the signal collecting unit in response to the corresponding medical data input units.

Figure 3:
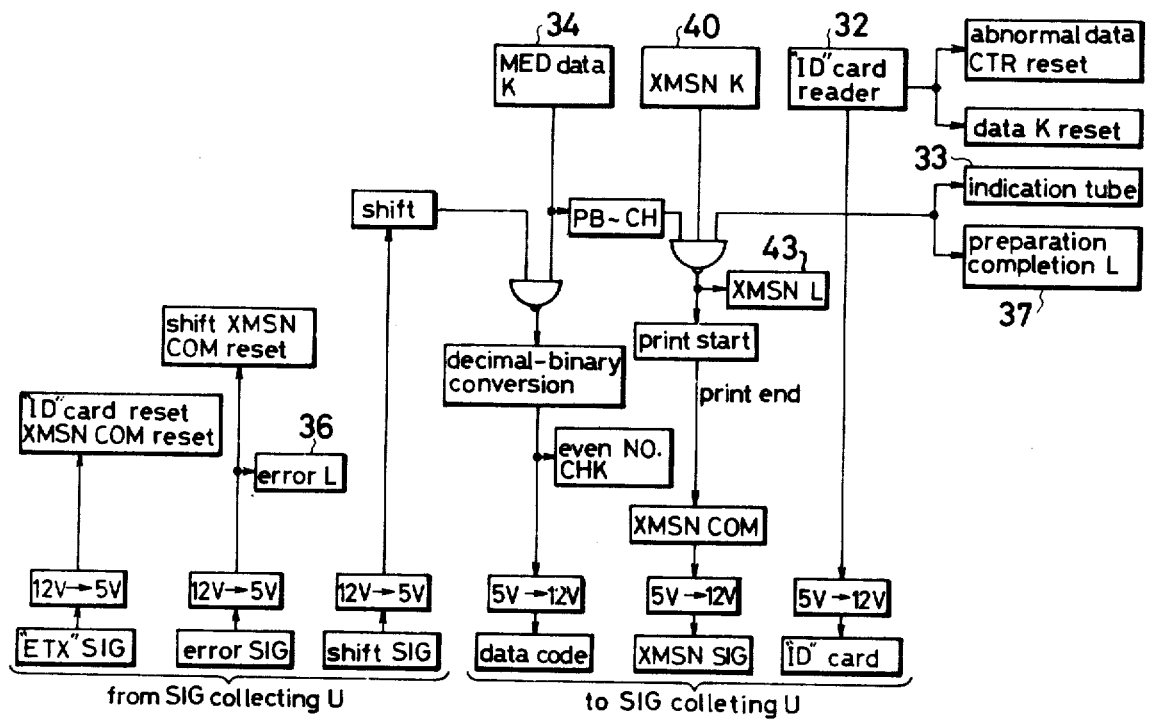
FIG. 3 is a block diagram illustrating in detail the medical data keyboard-printer of this invention.

FIG. 3 is a block diagram illustrating the operation of the medical data keyboard 30. When the ID card 41 is inserted into the ID card reader 32, medical data keys 34 and the counter for indicating abnormal data items are reset which cause identification tube 33 to indicate the individual identification number and the preparation completion lamp 37 to flash. The operator upon confirming the ID number of the individual person indicated on the indicating tube 33, sets the medical data key 34, and after having confirmed that the keys are locked, pushes the transmission key 40, so that visual records are printed by the printing unit 31 shown in FIG. 2, and the transmission signal for connecting into the signal collecting unit 10 is transmitted in response to the completion signal of the printing unit. The signal line is connected to the receiving circuit 11 of the signal collecting unit shown in FIG. 1, and the signal collecting unit upon receipt of the transmission signal from the input unit is enabled to accept the medical data from the input unit.

The signal collecting unit also works similarly in response to the transmission of signals from other medical data input units 20 and card reader 60. If there are errors contained in medical data, i.e., in ID code and data code, from the medical data input units 20 and card reader 60, the signal collecting unit 10 quits accepting the medical data, and returns the error signal to the data input unit which causes error lamp 36 to flash. After the medical data have been normally put into the signal collecting unit, the signal collecting unit 10 transmits an "ETX", end of transmission, signal to the data input units and disconnects the input units from the signal collecting unit. The ETX signal from the signal collecting unit causes the medical data keyboard unit 30 to turn off the transmission lamp 43 contained in the transmission key and, at the same time, releases the ID ard from the ID card reader.

Electrical signals are supplied at DC 12-volts among the signal collecting unit and various medical data input units; hence each of the signal collecting units and medical data input units has a converter for 5 volts to 12 volts and 12 volts to 5 volts. For example, the signal collecting unit and individual terminal units operate at an IC level of 5 volts.

Figure 4:
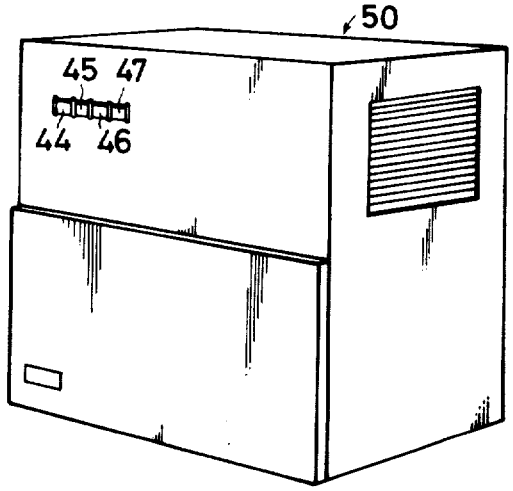
FIGS. 4 and 5 are perspective views of the interface unit which is a medical data input of the invention.
Figure 5:
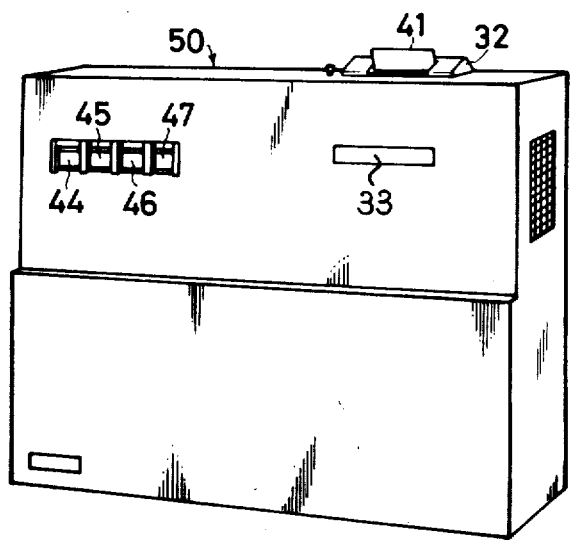

FIGS. 4 and 5 are perspective views of an embodiment of the interface unit 50 which is one of the medical data input units 20 of this invention. The interface unit 50 consists of six similar units, including an ID card reader for manually furnishing input of individual identification numbers for the ID card. These units are connected between each automatic device or data processing unit and the signal collecting unit. Each of these units also contains a power supply lamp 44, a power supply switch, an over-ride switch, an error lamp 45, a transmission lamp 46, and a retransmission key 47. The interface unit contains the interface control circuit, the input buffer memory domain, and the output gate, etc.

Like the medical data keyboard unit 30, the signal collecting unit 10 accepts the medical data from the individual interface units 50 connected to the receiving circuit 11. The signal collecting unit works in the same manner when receiving the medical data records from the card reader 60. However, when the data is being put into the card reader 60, the form of data contained in the card must be in the predetermined data code to contain the ID code which is an individual identification code; i.e., the data corresponds to every examination item. The cards may be punched or marked with the data.

Figure 6:
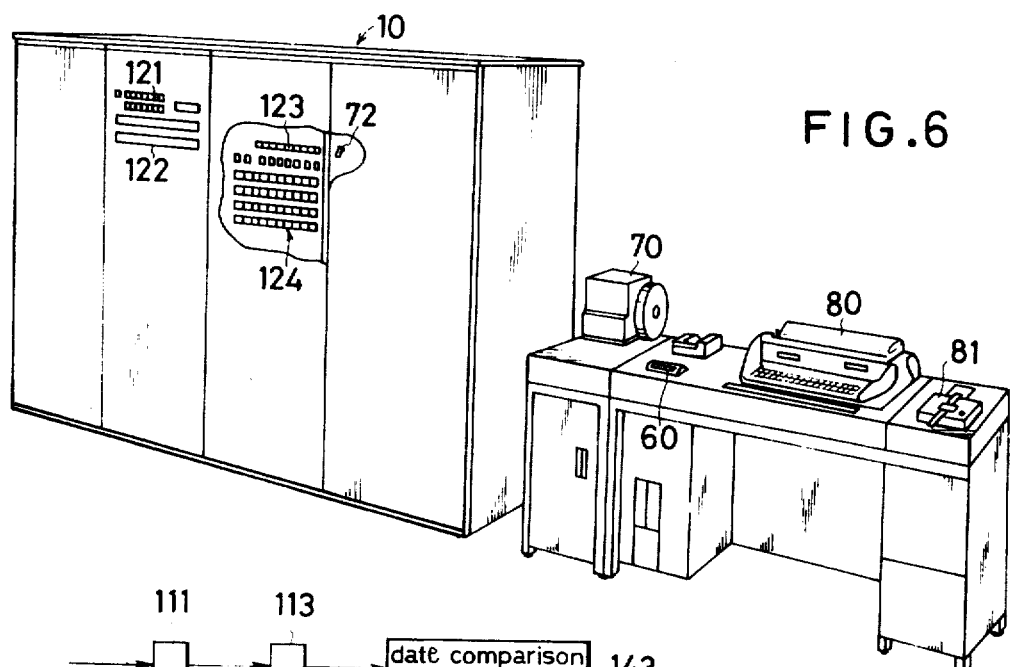
FIG. 6 is a perspective view showing the signal collecting unit, output unit, and printer keyboard unit for inquiry and an auxiliary card reader of the invention.

FIG. 6 shows an entire set up consisting of signal collecting unit 10, output unit 70 connected to the signal collecting unit, printing-keyboard unit 80, and card reader 60. The input unit 70 and the printer-keyboard unit 80 may be made in a variety of input-output unit forms such as conventional paper tape punchers, card punchers, or on-line printer-keyboard units. The printer-keyboard unit 80 includes a card reader 60 used for accepting medical data and a paper-tape puncher 81 which can be substituted for an output unit 70 when selected by means of a switch 72. The signal collecting unit 10 has a number of indicating lamps 121, a number of counter indicating tubes 122 for indicating the number of medical data inputs for every examination, a control panel 123 consisting of a number of control switches for controlling the data collecting system, and many digital switches 124 for setting a variety of conditions. The control panel 123 contains control switches for erasing all records in the memory unit, control switches for producing outputs of all data records in the memory unit, control switches for accepting the data which show the end of the medical data record in the memory unit. It also contains control switches for controlling the scanning of the receiving circuit 11 which controls the cutting-in of data from individual medical data input units 20, a reset switch for error indicating lamp, a control switch for the scanning circuit for the ouptut unit and printer-keyboard unit, a reset switch for the counter tube, and a general reset switch for the signal collecting unit and all switches are of the indication type. The signal collecting units 10 contains a power supply for the control citcuit, a power supply for the receiving circuit, a power supply for energizing the memory, a power supply for the output unit, and the memory. All of the power supplies are of the conventional type. The memory unit may be of a variety of types such as a conventional magnetic disc memory, for example.

Figure 7:
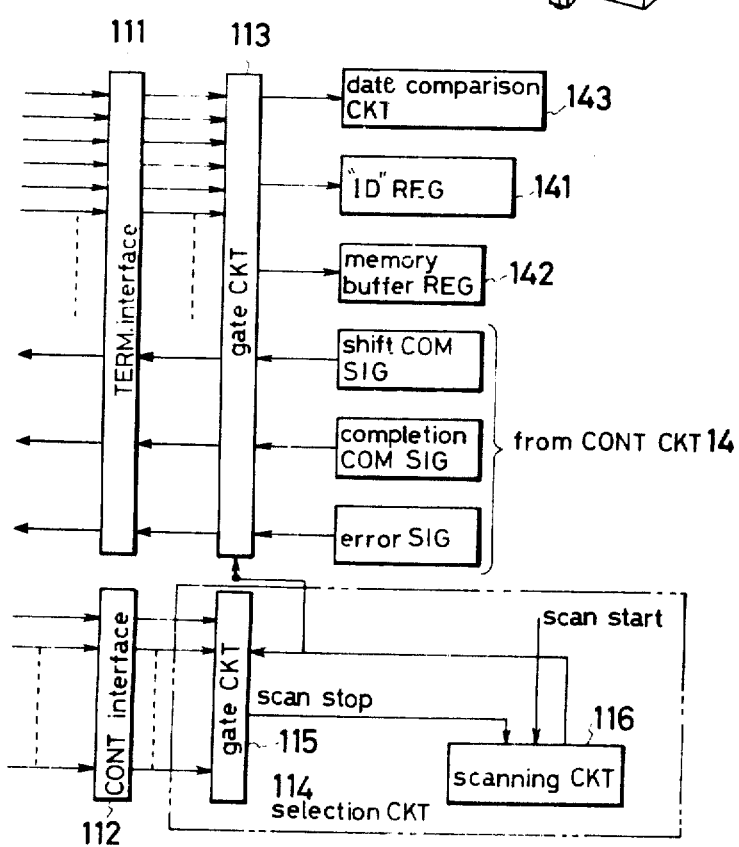
FIG. 7 is a block diagram illustrating the receiving circuit obtained in the signal collecting unit of the invention.

The receiving circuit 11 is shown in FIG. 7. The terminal interface 111 and control interface 112 are connected to the medical data input units and are connected to the gate circuit 113 and to the gate circuit 115 of the selection circuit 114, respectively. The scanning circuit 116 of the selection circuit 114 is connected to both the control switch for starting the scanning of the control panel 123 of FIG. 6 and the gate circuits 113 and 115, and has a second connection to the gate circuit 115.

The gate circuit 113 is connected to the terminal interface 111 and to memory unit peripheral circuits — data comparison circuit 143, ID register 141, memory buffer register 142 — scanning circuit of the selection circuit 114. It also has a second connection to the shift command signal line from the control circuit 14 of FIG. 1, and the completion command signal line, and the error signal line.

FIG. 8 illustrates the complete arrangement of peripheral circuits 18 composes of memories 13a, 13b and a variety of buffers, registers, counters, coincidence circuits, address set circuits for input applications, and a variety of buffers, registers, counters, and coincidence circuits for output applications. A variety of buffers, registers, counters, coincidence circuits, address set circuits of the memory unit peripheral circuits 18 are connected to many related control circuits of the control circuits 14. The control circuit 14 contains control circuits for space-clearing all addresses of memories 13a, 13b, control circuits for selecting the tracks of memories 13a, 13b, control circuits for transmitting the contents of the data buffer 145 to the memory 13a. Also control circuits for transmitting the contents of the data buffer 145 to the memory 13b, control circuits for transmitting and setting ETX signal in said address of the memory 13a, a control circuit for taking the data from the receiving circuit 11 to the memory buffer register 142 and transmitting the same data to the data buffer 145. Also included are a control circuit for reading the contents of the addresses of memories 13a, 13b, a control circuit for writing in said addresses of the memories 13a, 13b, a control circuit for selecting and preparing the data output needed for producing the medical data records in the memory 13 automatically in a predetermined form, and a control circuit for transmitting the data from the memory 13a to the output buffer memory domain of the memory 13b through the memory register 153.

In addition, a control circuit for transmitting the data from the output buffer memory domain of the memory 13b to the output unit 70, a control circuit for transmitting the data from the output buffer memory domain 167 of the memory 13b to the printer-keyboard 80, a control circuit for interlocking the output unit 70 and the printer-keyboard 80, and a control circuit for producing all medical data records of the memories 13a, 13b are provided.

There is also a control circuit for specifying and reading the track address of the memory 13a responsive to an inquiry from the printer-keyboard unit 80, and there is a control circuit for controlling the entire signal collecting unit 10.

The control circuit 14 is connected to the memories 13a, 13b, to the memory peripheral circuits 18, and to the receiving circuit 11.

The ID register 141 is connected to the ID signal line of the gate circuit 113. The receiving circuit 11 is connected to the data comparison circuit 143, queue registers 148, 149, and to the output ID register 150. It has a second connection to the ID register 151 and ID counter 152 which respond to the inquiry from the printer-keyboard 80, and the queue registers 148 and 149.

The memory buffer register 142 is connected to the data signal line from the gate circuit 113 of the receiving circuit 11 and is connected to the data buffer 145. The data buffer 145 is connected to the memory register 146, the A&Q data register 147 for selecting the data output and to the memory 13a, the memory register 153, and the memory 13b, and operates in connection with the data comparison circuit 143 which is connected to the ID register to select either one of the memories 13a or 13b so that the medical data will be stored.

The track selection counter 144 is connected to the date comparison circuit 143, to the address register 154, to the address register 155, to the address register 157, and to the indication lamp 160 for indicating "address over". The address register 154 is also connected to the address register 156 and to the address register 158. The address register 155, the address register 156, and the address register 157, respectively, are connected to the address register 159 which is connected to to the memory 13a.

The address register 156 is connected to the digital switch 161 for setting the ETX address.

The output ID register 150 is connected to the ID register 141 and is also connected to the digital switch 162 for setting the data and to the memory register 153. It is related to the data output set switch groups 163 and 164 which are set for selecting the data output that will be needed for automatically selecting the medical data setting coincidence circuits 165, 166, as well as the A&Q data register 147. The queue registers 148 and 149 are connected to the ID register 141.

An output scanning circuit 180 is connected to registers 181 and 182 through coincidence circuit 183.

Memory register 153 is connected to the memories 13a and 13b and is connected to the output buffer 167, and is related to the output buffer memory domain of the memory 13b. The output buffer 167 is connected to the memory register 153 and is connected to the output unit 70 and the printer-keyboard unit 80.

The output buffer 168 of the printer-kayboard unit 80 is connected to the inquiry command register 169 and to the ID register 151. The inquiry ID register 151 is connected to the address register 156, the address register 158, and the coincidence circuit 170 which compares the addresses of examination items.

The scanning circuit 180 which responds to an inquiry is related to the registers 181, 182, through the coincidence circuit 183.

The coincidence circuit 170 is connected to the inquiry ID register 151 and is also connected to the counter 171. The counter 171 is connected to the decoder 172, and the decoder 172 is connected to the examination item address set circuit 173.

Examination item address set circuit 172 is connected to the address registers 155, 156, and 157 and is related to the digital switch groups for setting the examination item address. The track selection counter 174 for inquiry is also connected to the address register 154.

The address set circuit 178 for data or other days is connected to the address register 177 and is related to the digital switch group for setting the addresses for data of other days.

The output buffer address set circuit 175 for ensuring the output buffer memory domain in the memory 13b is connected to the address register 176. The address register 179 is connected to the address registers 158, 176, and 177, and is connected to the memory 13b.

The memories 13a, 13b, and the memory peripheral circuit 18 accept various medical data from various medical data input units 20, and store it, and operate in a manner such as to automatically produce medical data records bases on the predetermined conditions, and also operate to produce specified medical data records responsive to an inquiry from the printer-keyboard unit 80. The memories 13a, 13b and the memory unit peripheral circuit 18 furthermore operate to produce all of the medical records contained in the memories 13a and 13b in response to the operating portion 12. These operations all relate to the control circuit 14. The memory addresses of medical data of a variety of examination items are identified with the individual medical data items and the ID of the individual persons being examined.

In operation, to obtain medical data on a particular day, the following occurs. First, an ID from the input unit 20 is introduced through the receiving circuit to the ID register 141, and the content of the ID is checked by means of the data comparison circuit 143. If an error is contained in the ID, the control circuit 14 transmits an error signal to the input unit and indicates address over 160. If the ID contains current information, a memory domain of medical data records is assured to the memory 13a by means of the control circuit 14, the track selection counter 144, the address register I 155, and the address register I 159.

At the same time, the data is received word by word one at a time from the input unit through the receiving circuit by means of the control circuit 14, the memory buffer register 142, the data buffer 145, and the memory register 146 until ETX is received, and such data are stored in the memory domain allocated previously in the memory 13a. Then, the input condition is confirmed by means of the control circuits 14 and the A&Q data register 147, the data output set switch group 163, data output set switch group 164, and the coincidence circuits 165 and 166, based on the data stored previously. When the setting conditions of the data output set switch group are satisfied, the corresponding ID signal is taken from the ID register 141 and supplied into the queue register 148 or 149. The queue registers 148 and 149, respectively, can hold the ID's of up to 16 persons.

When these operations are completed, the data collecting devide 10 cuts off the input unit 20. Then the control curcuit 14 confirms the presence or absence of input requirements from other input units. If such input requirements are present, the control circuit operates to take the data from the particular input unit, but if there is no input requirement, the control circuit energizes outputs or provides output to the monitor.

Where there is no input requirement, the following operation which produces an output is performed according to the priority order. Based on ID information contained in the queue registers 148 and 149, medical data records from the memory 13a are produced at the output unit 70 via the memory register 153, memory 13b, and output buffer 167, under control of the control circuit 14, the P & M registers 181 and 182, the coincidence circuit 183, the P & M scanning circuit 180, the ID register 141, the track selection counter 144, the address register 157, and the address register 159.

Also, in response to the inquiry from the printer keyboard unit 80, the signal collecting unit 10 performs the following operations. Based on the instruction word specified by the printer keyboard unit 80, the medical data records of the memory 13a and memory 13b are sent to the printer keyboard unit 80 via memory register 153, memory 13b, and output buffer 167, under control of the control circuit 14, the DTY buffer 168, the instruction register 169, the ID register 151, the coincidence circuit 170, the counter 171, and the decoder 172. The counters 152, 174, the ID register 141, the track selection counter 144, the address register 154, the address register 156, the address register 159, the inspection item address set circuit 173, the address register 155, the address register 157, the address register 158, and the address register 170 also perform this function.

Data from other days are stored in the memory 13b under control of the control circuit 14, the ID register 141, the track selection counter 144, the address register 154, the address register 158, the address register 170, the address set circuit 175, and the address register 176. In addition, the other day data address set circuit 178, and address register 177 aids in this function. These operations of input, output and monitor are under the control of the control circuit 14.

In this invention, unnecessary parts of a general-use process computer which have been used previously for the medical purposes are omitted, data available at examination locations are automatically fed to the interface. Where introduction of automated system is impossible the data keyboards are used. Also, the card reader is used to deal with conventional data. Individual ID identification is first put into the card reader and is recorded in the memory domain which is set individually in the signal collecting unit.

Thus, this invention allows much softwards to be omitted and reduces the time needed for preparing cards and sheets of data and avoids the possible loss of data while transmitting the data from the examination room to the data processing area, and also helps to reduce errors such as mispunching and mismarking at the time of preparing the data caused by an operator. With this invention expenses can be reduced to one-fifth of that using conventional methods operating with general-use comparators.

Although minor modifications might be suggested by those versed in the art, it should be understood that we wish to embody within the scope of the patent warranted hereon all such modifications as reasonably and properly come within the scope of our contribution to the art.

We claim as our invention:

1. Apparatus for collecting medical data comprising,
   a plurality of medical data input units each including a medical data keyboard with keys that can be set to establish desired medical tests, each of said input units including an identification card reader for receiving a patient identification means and including locking means for holding said identification means until a release signal is received,
   a plurality of patient test stations electrically connected to each of said medical data input unit to collect medical data from the patient whose identification means has been placed into said card reader,
   a central signal collecting and processing unit including a receiving circuit electrically connected to each of said plurality of medical data input units and including an identification register electrically connected to each of said identification card readers of said input units,
   a data comparison circuit connected to said identification register and comparing the information from said patient identification means with the desired patients identification and electrically connected to said input units to produce an enable signal or an identification error signal,
   an error indicator at each of said input units connected to said data comparison circuit,
   a control circuit in said processing unit connected to said receiving circuit,
   a plurality of memory cells in said processing unit and connected to said control circuit and said receiving circuit so as to store medical test data from said patient test stations,
   an end of test signal generator in said processing unit connected to said medical data input units and supplying an electrical signal to said card reader locking means to release said identification means at the end of medical tests, data output means connected to said processing means, and said control circuit connecting said memory cells to said output means to supply medical and identification data thereto which is reproduced by said output means.

2. Apparatus for collecting medical data according to claim 1 wherein said output means comprises a printer.

3. Apparatus for collecting medical data according to claim 1 including a plurality of queue registers in said processing unit connected to said receiving unit and control circuit to store data from a plurality of patients.

* * * * *